United States Patent
Yodfat et al.

(10) Patent No.: US 9,669,157 B2
(45) Date of Patent: *Jun. 6, 2017

(54) SKIN SECURABLE DRUG DELIVERY DEVICE WITH A SHOCK ABSORBING PROTECTIVE SHIELD

(71) Applicant: Roche Diagnostics Operations Inc., Indianapolis, IN (US)

(72) Inventors: Ofer Yodfat, Maccabim-Reut (IL); Ofer Arnold, Ha'movil (IL); Yair Dan, Moshav Kefar Kisch (IL)

(73) Assignee: Roche Diabetes Care, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/204,675

(22) Filed: Mar. 11, 2014

(65) Prior Publication Data

US 2014/0194818 A1 Jul. 10, 2014

Related U.S. Application Data

(63) Continuation of application No. 13/123,155, filed as application No. PCT/IL2009/000972 on Oct. 11, 2009, now Pat. No. 8,696,629.

(51) Int. Cl.
*A61M 5/142* (2006.01)
*A61M 5/14* (2006.01)

(52) U.S. Cl.
CPC ...... *A61M 5/14248* (2013.01); *A61M 5/1413* (2013.01); *A61M 2005/14264* (2013.01)

(58) Field of Classification Search
CPC ............. A61M 5/168; A61M 5/145; A61M 2005/14573; A61M 2005/14264
See application file for complete search history.

(56) References Cited

U.S. PATENT DOCUMENTS

| | | | |
|---|---|---|---|
| 3,631,847 A | 1/1972 | Hobbs, II | |
| 3,771,694 A | 11/1973 | Kaminski | |
| 4,498,843 A | 2/1985 | Schneider et al. | |
| 4,544,369 A | 10/1985 | Skakoon et al. | |
| 4,657,486 A | 4/1987 | Stempfle et al. | |
| 5,370,622 A | 12/1994 | Livingston et al. | |
| 5,472,317 A * | 12/1995 | Field ................. | A61M 5/14244 224/271 |
| 5,704,223 A * | 1/1998 | MacPherson et al. ......... | 62/3.62 |

(Continued)

FOREIGN PATENT DOCUMENTS

| WO | WO-99/65547 A1 | 12/1999 |
|---|---|---|
| WO | WO-01/58506 A2 | 8/2001 |

(Continued)

*Primary Examiner* — Imani Hayman
*Assistant Examiner* — James D Ponton
(74) *Attorney, Agent, or Firm* — Dinsmore & Shohl LLP

(57) ABSTRACT

Disclosed is a skin securable therapeutic fluid dispensing device that includes a reservoir adapted to retain therapeutic fluid, a pump driving mechanism, and at least one housing configured to accommodate the reservoir and the pump driving mechanism, with at least a portion of the at least one housing defining at least a portion of the reservoir. The device also includes a shield coupled to the at least one housing, the shield configured to protect, at least in part, the reservoir from application of external forces thereon.

15 Claims, 17 Drawing Sheets

(56) References Cited

U.S. PATENT DOCUMENTS

| | | | |
|---|---|---|---|
| 5,957,895 | A | 9/1999 | Sage et al. |
| 6,485,461 | B1 | 11/2002 | Mason et al. |
| 6,589,229 | B1 | 7/2003 | Connelly et al. |
| 6,723,072 | B2 | 4/2004 | Mahoney et al. |
| 6,740,059 | B2 | 5/2004 | Flaherty |
| 7,736,344 | B2* | 6/2010 | Moberg et al. ............... 604/232 |
| 2001/0034502 | A1* | 10/2001 | Moberg .............. A61M 5/1456 604/154 |
| 2003/0110595 | A1* | 6/2003 | Collins .................... A45F 5/02 24/3.12 |
| 2004/0004680 | A1 | 1/2004 | Kim |
| 2004/0183511 | A1* | 9/2004 | Dening ........................ 323/282 |
| 2007/0106218 | A1 | 5/2007 | Yodfat et al. |
| 2007/0191702 | A1 | 8/2007 | Yodfat et al. |
| 2008/0215035 | A1 | 9/2008 | Yodfat et al. |
| 2009/0143735 | A1 | 6/2009 | De Polo et al. |

FOREIGN PATENT DOCUMENTS

| | | |
|---|---|---|
| WO | WO-03/099351 A2 | 12/2003 |
| WO | WO-2006/089958 A1 | 8/2006 |
| WO | WO-2008/077914 A2 | 7/2008 |
| WO | WO-2009013736 A1 | 1/2009 |
| WO | WO-2009016636 A2 | 2/2009 |
| WO | WO-2009125398 A2 | 10/2009 |

* cited by examiner

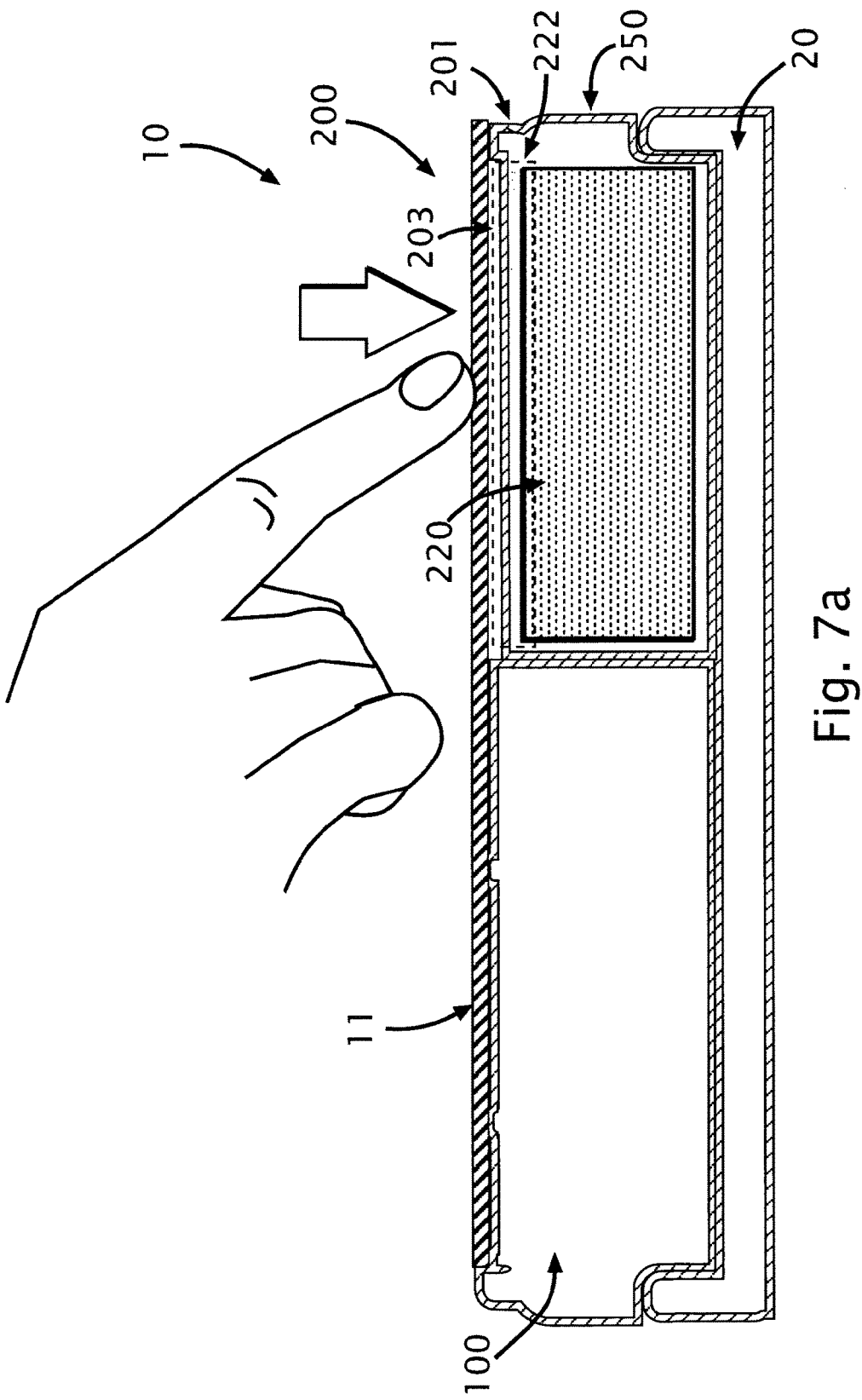

SKIN SECURABLE DRUG DELIVERY DEVICE WITH A SHOCK ABSORBING PROTECTIVE SHIELD

CROSS-REFERENCE TO RELATED APPLICATIONS

The present application is a continuation of U.S. patent application Ser. No. 13/123,155 filed Apr. 7, 2011, which is a 35 U.S.C. §371 national stage entry of PCT/IL2009/000972, which has an international filing date of Oct. 11, 2009 and claims the benefit of U.S. Provisional Patent Application No. 61/103,383, filed on Oct. 7, 2008. The present application incorporates herein by reference the contents of each of the above-referenced applications in their entireties.

FIELD OF THE DISCLOSURE

The present disclosure relates generally to a device for sustained infusion of fluids. More particularly, the disclosure relates to a device that includes a skin securable unit comprising a reusable part and a disposable part. Even more particularly, the present disclosure relates to a two part skin securable device that includes a protective shield.

BACKGROUND

Medical treatment of several illnesses requires continuous drug infusion into various body compartments, such as subcutaneous and intra-venous injections. Diabetes mellitus (DM) patients, for example, require the administration of varying amounts of insulin throughout the day to control their blood glucose levels. In recent years, ambulatory portable insulin infusion pumps have emerged as a superior alternative to multiple daily syringe injections of insulin, initially for Type 1 diabetes patients and subsequently for Type 2 diabetes patients. These pumps, which deliver insulin at a continuous, or periodic, basal rate as well as in bolus volumes, were developed to liberate patients from repeated self-administered injections, and allow them to maintain a near-normal daily routine. Both basal and bolus volumes must be delivered in substantially precise doses, according to individual prescription, because an overdose or underdose of insulin could be fatal.

The first generation of portable insulin pumps includes "pager like" devices, each with a reservoir contained within a rigid case housing. The reservoir is usually a syringe barrel and reservoir filling is performed by drawing replenishing therapeutic fluid from a vial with a complementary adapter. After filling the reservoir, the syringe handle (plunger rod) is disconnected and disposed of, and the barrel (reservoir) is placed within the rigid case housing. The proximal end of the reservoir is engaged with a driving mechanism and its distal end is connected to an infusion set (tubing). Examples of such devices are disclosed, for example, in U.S. Pat. Nos. 3,631,847, 3,771,694, 4,657,486 and 4,544,369, the contents of all of which are hereby incorporated by reference in their entireties. These devices represent an improvement over the application of multiple daily injections, but suffer from some drawbacks, among which are the devices' relatively large size, weight, and long tubing.

To avoid the limitations of first generation infusion pumps, a new concept was proposed, which was implemented in second generation pumps. The new concept concerns a remote controlled skin adherable device with a rigid case housing having a bottom surface adapted to be in contact with the patient's skin. The reservoir is contained within the rigid case housing and reservoir filling is performed with an additional syringe that is used to draw the replenishing therapeutic fluid (the drug) from a vial with an injection needle that is also adapted to be in fluid communication with the reservoir. This approach is described, for example, in U.S. Pat. Nos. 4,498,843, 5,957,895, 6,589,229, 6,740,059, 6,723,072 and 6,485,461, the contents of all of which are hereby incorporated by reference in their entireties. These second generation skin adherable devices also have several drawbacks including, for example, the fact that an entire second-generation device, including all the expensive components (electronics, a driving mechanism, etc.), has to be disposed of every 2-3 days.

Third generation skin-adherable devices were developed to avoid the cost issues of second generation devices and to extend patient customization. An example of such a device is described in co-owned/co-pending U.S. patent application Ser. No. 11/397,115 (Publication No. 2007/0106218), the content of which is hereby incorporated by reference in its entirety. Such a third generation device includes a remote control (also referred to as a remote control unit and/or a remote controller) and a skin-securable (e.g., adherable) dispensing unit (also referred to as a patch and/or a patch unit) that includes two parts: (1) a reusable part containing the electronics, at least a portion of the driving mechanism and other relatively expensive components, and (2) a disposable part containing, for example, the reservoir and/or relatively inexpensive components.

A skin-securable fluid delivery device to deliver therapeutic fluid (e.g., insulin) is disclosed, for example, in co-owned/co-pending U.S. patent application Ser. No. 11/989,681, filed Jul. 24, 2007, and claiming priority to U.S. Provisional Patent Applications Nos. 60/833,110, filed Jul. 24, 2006, and 60/837,877, filed Aug. 14, 2006, both of which are entitled "Systems, Devices, and Methods for Fluid/Drug Delivery", the contents of all of which are hereby incorporated by reference in their entireties.

A fourth generation infusion device was developed that includes a dispensing unit that can be disconnected and reconnected to a skin-adherable cradle unit (also referred to as a cradle) and may be operated by a user interface (an interface that includes, for example, buttons/switches) located, for example, on the reusable part. Such a fourth (4th) generation device is described, for example, in: I) co-owned/co-pending U.S. patent application Ser. No. 12/004,837 (Publication No. 2008/0215035), filed Dec. 20, 2007, claiming priority to U.S. Provisional Patent Application No. 60/876,679, filed Dec. 22, 2006, entitled "Systems, Devices, and Methods for Sustained Delivery of a Therapeutic Fluid", the contents of which are hereby incorporated by reference in their entireties; 2) co-owned/co-pending International Patent Application No. PCT/IL08/001001 (Publication No. WO2009/013736), filed Jul. 20, 2008, claiming priority to U.S. Provisional Patent Application No. 60/961,527, and entitled "Manually Operable Portable Infusion Pump", the contents of which are hereby incorporated by reference in their entireties; and 3) co-owned/co-pending International Patent Application No. PCT/IL08/001057 (Publication No. WO2009/016636), filed Jul. 31, 2008, claiming priority to U.S. Provisional Applications Nos. 60/963,148 and 61/004,019, and entitled "Portable infusion device with means for monitoring and controlling fluid delivery", the contents of all of which are hereby incorporated by reference in their entireties.

Third (3rd) and fourth (4th) generation dispensing units may be equipped with an analyte (i.e. glucose) sensor to enable continuous (or near-continuous) and/or periodic measurements/readings of analyte levels. Fluid dispensing may thus be performed automatically according to analyte sensing (closed loop system) or performed semi-automatically if the user wishes to have some control of the delivery operations (e.g., open loop system). A fourth (4th) generation sensing and dispensing device is described, for example, in co-owned/co-pending U.S. patent application Ser. No. 11/706,606 (Publication No. 2007/0191702), the content of which is hereby incorporated by reference in its entirety.

An example of a pumping mechanism of third (3rd) and fourth (4th) generation two-part skin-securable dispensing units is a "syringe-like mechanism". A plunger (piston) is configured to slide within a barrel (reservoir), thus pushing the drug outwardly. The plunger is displaced by, for example, a threaded rod (plunger rod) that can be rigidly connected to the plunger or articulately interact with the plunger and rotate freely. The threaded plunger rod may also used to backwardly slide the plunger during reservoir filling. After filling, the disposable part that contains the reservoir and the outlet port is connected to the reusable part.

Unlike first (1g) and second (2"d) generation pumps, the reservoir may not be protected within a rigid case housing because the reservoir walls correspond to at least a part of the walls of the disposable part, and neither is contained within an additional protective rigid case housing. Such an unprotected reservoir could endanger the user if a high force or impact is directly applied to the dispensing unit and the reservoir walls, thus causing drug overflow (and consequently overdose).

SUMMARY

In view of the foregoing, in some embodiments, a device that includes a skin securable drug dispensing unit with a reservoir protection mechanism and a method to avoid drug overflow are disclosed.

In some embodiments, a device that includes a skin securable insulin dispensing unit with a reservoir protection mechanism and a method to avoid insulin overflow are disclosed.

In some embodiments, a device that includes a skin securable insulin dispensing unit with a reservoir protection mechanism that continuously (or periodically) monitors body glucose levels (e.g., in the blood, in the interstitial fluid ("ISF")) and can dispense insulin according to glucose levels (i.e., closed and open loop system implementations), and a method to avoid insulin overflow, are disclosed.

In some embodiments, a skin securable insulin dispensing unit with a reservoir protection mechanism which is miniature, discreet, economical for the users and cost effective, and a method to avoid insulin overflow, are described.

In some embodiments, a skin-securable insulin dispensing unit with a reservoir protection mechanism that can be remotely controlled, and a method to avoid insulin overflow, are described.

In some embodiments, a skin-securable insulin dispensing unit with a reservoir protection mechanism that can be operated manually by buttons/switches located on the dispensing unit, and a method to avoid insulin overflow, are described.

In some embodiments, a device that includes skin securable insulin dispensing unit, including a reservoir protection mechanism, with the dispensing unit being composed of two parts, namely, a reusable part and a disposable part, and a method to avoid insulin overflow, are disclosed.

In some embodiments, a device that includes a skin securable insulin dispensing unit, including a reservoir protection mechanism, with the dispensing unit being composed of a reusable part and a disposable part, the disposable part containing an energy supply, and a method to avoid insulin overflow, are described.

In some embodiments, a device that includes a skin-securable insulin dispensing unit with a reservoir protection mechanism is described. The dispensing unit may be composed of two parts, namely, a reusable part and a disposable part, and may further include a "syringe-like" pumping mechanism, i.e. a syringe reservoir with a propelling plunger. The syringe barrel, plunger, and threaded plunger rod may be contained within the disposable part, and a pump driving mechanism that may include, for example, a motor and a gear assembly may be contained within the reusable part. Also described is a method to avoid insulin overflow.

In some embodiments, a device that includes a skin securable insulin dispensing unit with a reservoir protection mechanism that can be disconnected and reconnected to a skin adherable cradle unit, and a method to avoid insulin overflow, are disclosed.

The current disclosure describes a device that delivers therapeutic fluid (e.g., insulin) into the body. In some embodiments, the device comprises the following three units: a two-part dispensing unit, a skin-securable (e.g., adherable) cradle unit (hereinafter "cradle") and a remote control (hereinafter "RC"). The dispensing unit can be disconnected and reconnected from and to the cradle. A connecting lumen provides fluid communication between the dispensing unit and a subcutaneous cannula that is rigidly connected to the cradle. Fluid delivery can be remotely controlled by the RC or by manual buttons located on the dispensing unit.

Below is a description of each unit:
1—A dispensing unit: may include a pumping mechanism, a reservoir and an outlet port. The dispensing unit may be configured as a single part that includes a reservoir, one or more batteries, electronics, and a pumping mechanism. Alternatively, the dispensing unit may be configured as a two-part dispensing unit that comprises:
   a. A reusable part (the "RP") containing a motor, electronics, and other relatively expensive components.
   b. A disposable part (the "DP") containing the reservoir, the outlet port, and, in some embodiments, a power source, such as one or more batteries.
2—A cradle: a substantially flat plate with an adhesive layer facing the skin. The cradle may be provided with a passageway to allow subcutaneous insertion of a cannula, and locking mechanisms (e.g., snaps, latches, etc.) to secure the cannula and the dispensing unit to the cradle.
3—A remote control (RC): a handheld piece for receiving, transmitting and/or generating programming instructions and commands to control, for example, fluid flow, control the dispensing unit, data acquisition, and indications (e.g., display). In some embodiments, the RC may be implemented as or using a wrist-watch, cellular phone, PDA, iPhone, iPod, laptop, etc.

In some embodiments, fluid delivery is performed using a syringe-type mechanism. A sliding plunger moves forward by a motor driven threaded plunger rod. The plunger rod may be manually actuated to move the plunger backward during reservoir filling.

In some embodiments, the reservoir has a flat profile (e.g., oval, ellipse, four arches, etc.) to facilitate maintaining a thin DP configuration.

A protecting plate (hereinafter a "shield") is provided to protect the reservoir from external forces and impact, to thus prevent unintentional fluid overflow (that could cause overdosing). The shield may be connected to the RP and is placed above the reservoir during DP-RP connection.

Thus, in some embodiments of the present disclosure, a device for medical infusion of fluids into the body that includes a reservoir contained within a dispensing unit that is protected from external force and impact is provided.

In some embodiments, a two-part dispensing unit comprising a reusable part and a disposable part is provided. The reusable part contains motor, electronics, and other relatively expensive components and the disposable part includes, for example, a reservoir and an outlet port. A power source (e.g., batteries) may reside in the disposable part and/or in the reusable part. A shield may be coupled to the RP and configured to protect the reservoir from external forces and impact.

In some embodiments, a dispensing unit for sustained medical infusion with controlled rate injection of therapeutic fluid into a body is provided.

In some embodiments, a dispensing unit that is thin, has no external tubing and can be connected to any part of the body is provided.

In some embodiments, a device for medical infusion that contains a skin adherable cradle with a passageway for a subcutaneous cannula and a locking mechanism (e.g., snaps) to rigidly secure the dispensing unit and to enable disconnection and reconnection of the dispensing unit from and to the cradle is described.

In some embodiments, a dispensing unit is provided. Infusion programming may be performed by a remote control or by at least one control button located on the dispensing unit.

In some embodiments, a device for infusion of a fluid into the patient's body through a flexible soft cannula is provided.

In some embodiments, a skin securable therapeutic fluid dispensing device is provided. The device includes a reservoir adapted to retain therapeutic fluid, a pump driving mechanism, and at least one housing configured to accommodate the reservoir and the pump driving mechanism, with at least a portion of the at least one housing defining at least a portion of the reservoir. The device also includes a shield coupled to the at least one housing, the shield configured to protect, at least in part, the reservoir from application of external forces thereon.

Embodiments of the device may include any of the following features.

The device may further include a reusable part including at least a portion of the pump driving mechanism and a reusable part housing configured to accommodate the at least a portion of the pump driving mechanism. The device may further include a disposable part coupleable to the reusable part. The disposable part may include the reservoir, and a disposable part housing configured to accommodate the reservoir, at least a portion of the disposable part housing may define at least a portion of the reservoir. The shield may be coupled to at least one of, for example, the reusable part housing and/or the disposable part housing. The at least one housing may include the reusable part housing and the disposable part housing.

The reusable part housing may include at least one protrusion receivable within a corresponding at least one opening provided on the shield to enable proper alignment of the shield.

The reusable part housing may be provided with a rim having a contour substantially matching a contour defined by edges of the shield to enable proper alignment of the shield.

The disposable part may further include a frame provided on or adjacent to the disposable part housing, the frame configured to support the shield such that the shield is not in direct contact with the at least the portion of the disposable part housing defining the at least the portion of the reservoir.

The shield may be integral with the reusable part housing.

At least part of the device may be removably connectable to a cradle, the cradle may include an adhesive layer on one or more surfaces of the cradle to adhere to a skin of a patient and a passageway for subcutaneously inserting a cannula therethrough.

The disposable part may further include a frame provided on or adjacent to the disposable part housing, the frame configured to support the shield such that the shield is not in direct contact with the at least a portion of the disposable part housing defining the at least the portion of the reservoir. The frame may further be configured to divert applied external forces to the cradle.

The shield may be integral with the disposable part housing.

The shield may be coupled to the at least one of, for example, the reusable part housing and/or the disposable part housing such that an air gap is defined between the shield and the at least the portion of the disposable part housing defining the at least the portion of the reservoir.

The shield may be manufactured from one or more of, for example, a metal and/or a polycarbonate material.

The shield may be configured to prevent penetration of radiation into the device.

The shield may include at least one of, for example, a display and/or one or more control buttons.

The reservoir may have a cross-section selected from a group consisting of: oval, elliptical, rectangular and multi-curved.

In some embodiments, a skin securable therapeutic fluid dispensing device is provided. The device includes a dispensing unit having at least one housing configured to accommodate at least a pump driving mechanism and a reservoir retaining therapeutic fluid. At least a portion of the at least one housing defines at least a portion of the reservoir. The device further includes a cradle including an adhesive layer on one or more surfaces of the cradle to adhere to skin of a patient, and a passageway for subcutaneously inserting a cannula therethrough. The cradle is configured to enable removable coupling of the dispensing unit thereto, and a shield coupled to at least one of, for example, the dispensing unit and/or the cradle. The shield is configured to protect, at least in part, the reservoir from application of external forces.

Embodiments of the device may include one or more of the above-described features of the first device, as well as any of the following features.

The shield may further be configured to divert the applied external forces to the cradle.

The dispensing unit may further include a reusable part including at least a portion of the pump driving mechanism and a reusable part housing configured to accommodate the at least a portion of the pump driving mechanism. The dispensing unit may further include a disposable part coupleable to the reusable part, the disposable part including the reservoir and a disposable part housing configured to accommodate the reservoir, at least a portion of the disposable part housing defining at least a portion of the reservoir. The at least one housing may include the reusable part housing and the disposable part housing.

One or more of the at least one housing may include at least one protrusion receivable within a corresponding at least one opening provided on the shield to enable proper alignment of the shield.

One or more of the at least one housing may be provided with a rim having a contour substantially matching a contour defined by edges of the shield to enable proper alignment of the shield.

The dispensing unit may further include a frame provided on or adjacent to one or more of the at least one housing, the frame configured to support the shield such that the shield is not in direct contact with the at least the portion of the at least one housing defining the at least the portion of the reservoir.

The frame may further be configured to divert applied external forces to the cradle.

The shield may be integral with the dispensing unit.

The shield may be coupled to the dispensing unit such that an air gap is defined between the shield and the at least the portion of the at least one housing defining the at least the portion of the reservoir.

The shield may be coupled to the cradle via a hinge.

At least one of, for example, the cradle and/or the shield may further include at least one lock for locking the shield to the cradle upon coupling the dispensing unit to the cradle, the at least one lock being further configured to enable release of the dispensing unit from the cradle upon actuation of the at least one lock by a user.

In some embodiments, a skin securable therapeutic fluid dispensing device is disclosed. The device includes a dispensing unit having at least one housing configured to accommodate at least a pump driving mechanism, a cradle including a reservoir retaining therapeutic fluid and an adhesive layer on one or more surfaces of the cradle to adhere to skin of a patient, the cradle configured to enable removable connection of the dispensing unit thereto. The device also includes a shield coupled to at least one of the dispensing unit and the cradle, the shield configured to protect, at least in part, the reservoir from application of external forces.

Embodiments of the device may include one or more of the above-described features of the first and second devices.

In some embodiments, a method of providing therapeutic fluid to a user via a skin securable therapeutic fluid dispensing device is disclosed. The method includes providing the skin securable therapeutic fluid dispensing device, the device having at least one housing configured to accommodate at least a pump driving mechanism and a reservoir adapted to retain the therapeutic fluid, at least a portion of the at least one housing defines at least a portion of the reservoir. The method also includes placing the therapeutic fluid in the reservoir and providing a shield adjacent to at least the portion of the at least one housing defining the at least the portion of the reservoir, the shield being configured to be substantially uncompromising such that forces applied to the dispensing device, either within or outside the vicinity of the reservoir area, do not compromise the structure of the dispensing device and/or the reservoir. The method further includes dispensing the therapeutic fluid from the reservoir.

Embodiments of the method may include one or more of the above-described features of the devices, as well as any of the following features.

The shield may be coupled to the at least one housing of the dispensing device.

The method may further include coupling the dispensing device to a cradle, the cradle having an adhesive layer on one or more surfaces of the cradle to adhere to a skin of a patient and a passageway for subcutaneously inserting a cannula therethrough.

The method may further include providing a frame on or adjacent to one or more of the at least one housing of the dispensing device, the frame configured to support the shield such that the shield is not in direct contact with the at least the portion of the at least one housing defining the at least the portion of the reservoir.

The method may further include coupling the dispensing device to a cradle, the cradle having an adhesive layer on one or more surfaces of the cradle to adhere to a skin of a patient and a passageway for subcutaneously inserting a cannula therethrough, and diverting to the cradle, by the frame, applied external forces.

The shield may be coupled to the cradle via a hinge.

The shield may be coupled to the at least one housing of the dispensing device such that an air gap is defined between the shield and the at least the portion of the at least one housing defining the at least the portion of the reservoir.

The dispensing device may include a reusable part and a disposable part coupleable to the reusable part. The method may further include coupling the disposable part to the reusable part.

In some embodiments, a method of providing therapeutic fluid to a user via a skin securable therapeutic fluid dispensing device is provided. The method includes providing the skin securable therapeutic fluid dispensing device, the device comprising a disposable part including a disposable part housing, and a reusable part connectable to a disposable part, at least a portion of the disposable part housing defining at least a portion of a reservoir. The method also includes placing the therapeutic fluid in the reservoir of the disposable part, and providing a shield adjacent to at least the portion of the disposable part housing defining the at least the portion of the reservoir, the shield being configured to be substantially uncompromising such that forces applied to the disposable part, either within or outside the vicinity of the reservoir area, do not compromise the structure of the disposable part and/or the reservoir. The method further includes dispensing the therapeutic fluid from the reservoir.

Embodiments of the method may include one or more of the above-described features of the devices and the first method.

Details of one or more implementations are set forth in the accompanying drawings and in the description below. Further features, aspects, and advantages will become apparent from the description, the drawings, and the claims.

BRIEF DESCRIPTION OF DRAWINGS

FIGS. 7a-7b are cross sectional diagrams of a dispensing unit protected by a shield and connected to a cradle such that external force applied on the shield are diverted from the reservoir to the dispensing unit's rigid edges.

DETAILED DESCRIPTION

Figure 1:
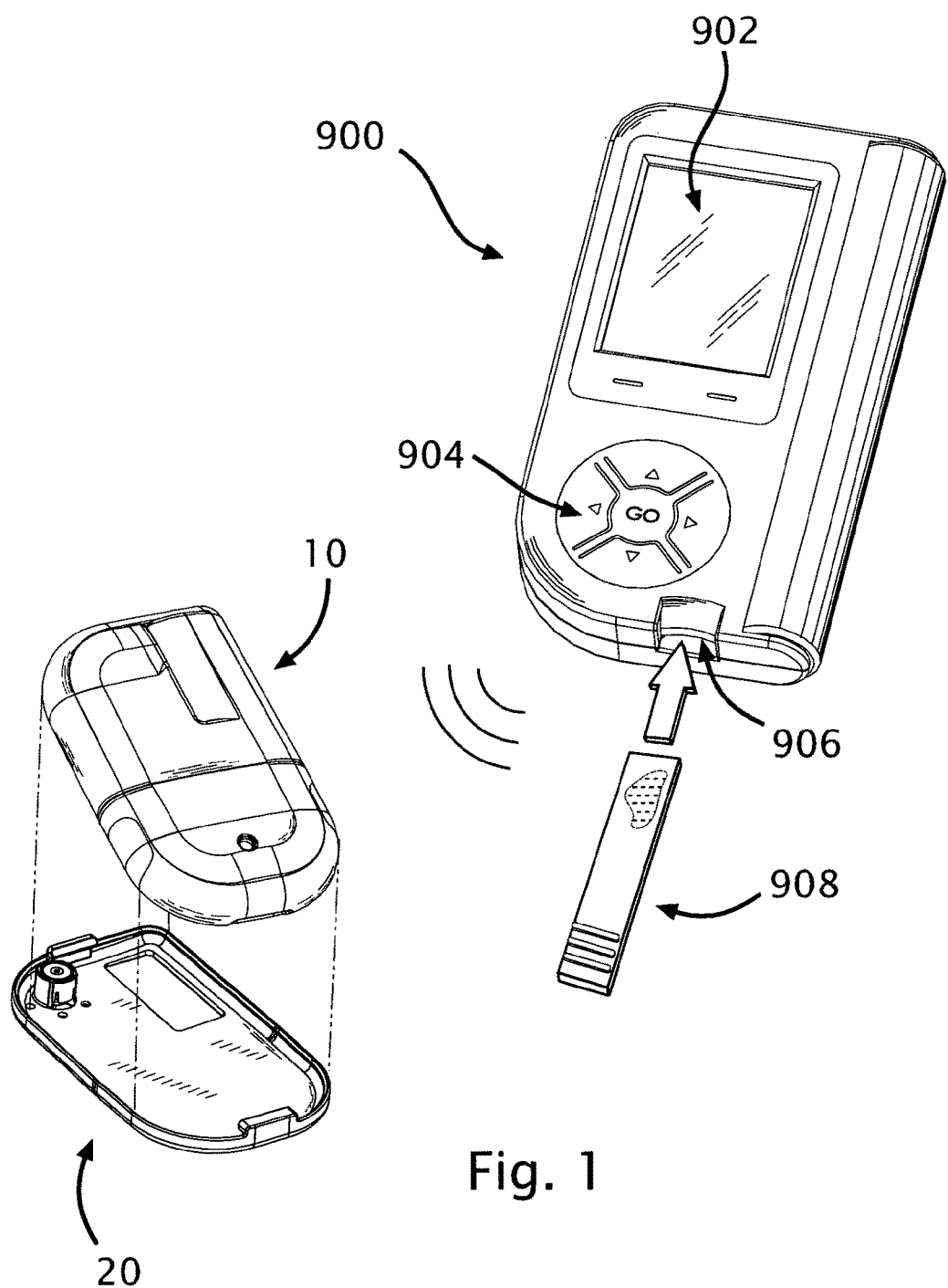
FIG. 1 are diagrams and views of an infusion (dispensing) device that includes a remote control ("RC"), a two part skin securable dispensing unit and a skin adherable cradle unit ("cradle").

Referring to FIG. 1, diagrams of an infusion/dispensing device that may include three (3) units are shown. The three units may include, for example:

A dispensing unit 10 that can comprise one or two parts. The dispensing unit can be disconnected and reconnected from and to a skin securable (e.g., adherable) cradle 20. Commands/instructions to control fluid dispensing and other operations can be performed by buttons located on the dispensing unit, as disclosed, for example, in co-owned, co-pending International Patent Application No. PCT/IL08/001001 (Publication No. WO2009/013736) and International Patent Application No. PCT/IL08/001057 (Publication No. WO2009/016636), the contents of all of which are hereby incorporated by reference in their entireties.

A remote control 900 ("RC") that may include, for example, an integrated blood glucose monitor. The RC includes a screen 902, a keypad 904, and it may further include a slot 906 to receive a blood test strip 908. The RC 900 is used, for example, for dispensing unit programming and data acquisition, and for communicating with other electronic devices such as, for example, a PC, to perform data downloading and uploading.

The cradle 20 that, in some embodiments, is a substantially flat plate or platform with a passageway that includes skin adhesive at its bottom and a locking mechanism or connectors (e.g., snaps) to rigidly secure the dispensing unit 10 and a cannula to the cradle. In some embodiments, the cradle 20 may include the reservoir retaining the therapeutic fluid (not shown).

An example of a device such as that depicted in FIG. 1 is disclosed in co-owned/co-pending U.S. patent application Ser. No. 12/004,837 (Publication No. 2008/0215035) the content of which is hereby incorporated by reference in its entirety. Such a device is further disclosed in co-owned, co-pending U.S. patent application Ser. No. 11/397,115 (Publication No. 2007/0106218), and in co-owned, co-pending International Patent Application No. PCT/IL09/000388, filed Apr. 7, 2009, entitled "Systems, devices and methods for fluid delivery", the contents of all of which are hereby incorporated by reference in their entireties.

Co-owned/co-pending U.S. patent application Ser. No. 11/706,606 (Publication No. 2007/0191702), the content of which is hereby incorporated by reference in its entirety, discloses a device that includes a dispensing unit (e.g., an insulin dispensing unit) and an analyte sensor (e.g., a continuous glucose monitor). This type of dual function device has a similar configuration to that outlined above and can also be disconnected and reconnected from and to the skin at patient's discretion.

Figure 2:
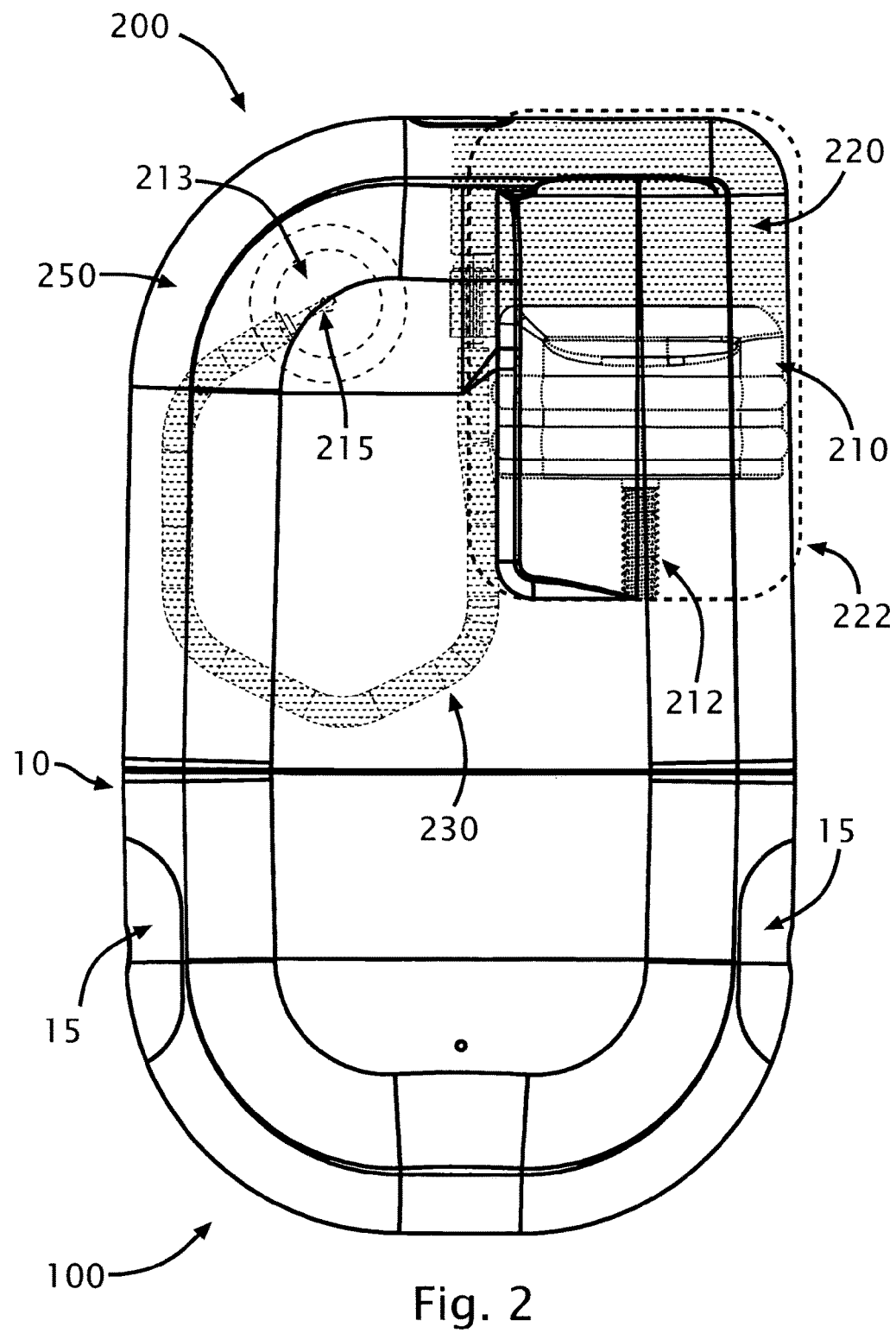
FIG. 2 is a diagram of a two part dispensing unit including a reusable part (RP) and a disposable part (DP).

Referring to FIG. 2, a diagram of a dispensing unit 10 comprising two parts, a reusable part 100 ("RP"), and a disposable part 200 ("DP"), is shown. The dispensing unit 10 may employ, in some embodiments, a pumping mechanism implemented as a "syringe-like" mechanism that includes a sliding plunger within a barrel (reservoir). The RP may contain the relatively expensive components including, but not limited to, a pump driving mechanism that includes, for example, a motor and a gear arrangement, electronic modules ( shown in FIG. 6A), and buttons 15 to enable manual control of fluid delivery operations without the RC. The DP 200 contains a reservoir 220, a plunger 210 with one or more gaskets, a threaded plunger rod 212 (shown only partially in FIG. 2), a delivery tube 230, an outlet port 213, and a connecting lumen 215. The DP 200 may also include, in some embodiments, one or more batteries (not shown). Forward motion of the plunger 210 urges fluid from the reservoir 220 to the connecting lumen 215 through the delivery tube 230. The reservoir's cross-sectional shape may be, in some embodiments, rectangular, oval, elliptical, or may include a plurality of arches/curves (e.g., four or eight arches/curves), which may have having at least two different radii, to facilitate maintaining a low profile of the dispensing unit 10 (i.e., relatively thin dimensions). The DP 200 may include a shell or exterior 250 to house internal components. At least some of the surfaces of the shell 250 may define the walls of the reservoir. An "insert" (chassis, not shown) may support the delivery tube 230, the connecting lumen 215 and the one or more batteries, and may also serve as a construction reinforcing mechanism. The area 222, also referred-to as "jeopardized zone" (encircled by a dashed line), is generally not supported/reinforced by the insert, and thus is pressure-sensitive and might be vulnerable to external forces. For example, large external force exertions or a sudden impact might squeeze the reservoir and cause an unintentional fluid delivery which may result in drug overdose. This risk may be further aggravated due to the low profile, "non round" ("non circular") shape of the reservoir (e.g., as is the case with a reservoir having an oval-shaped cross-section). In some embodiments, the jeopardized zone 222 is a portion of the shell 250 which defines at least a portion of the reservoir 220.

Figures 3A, 3B:
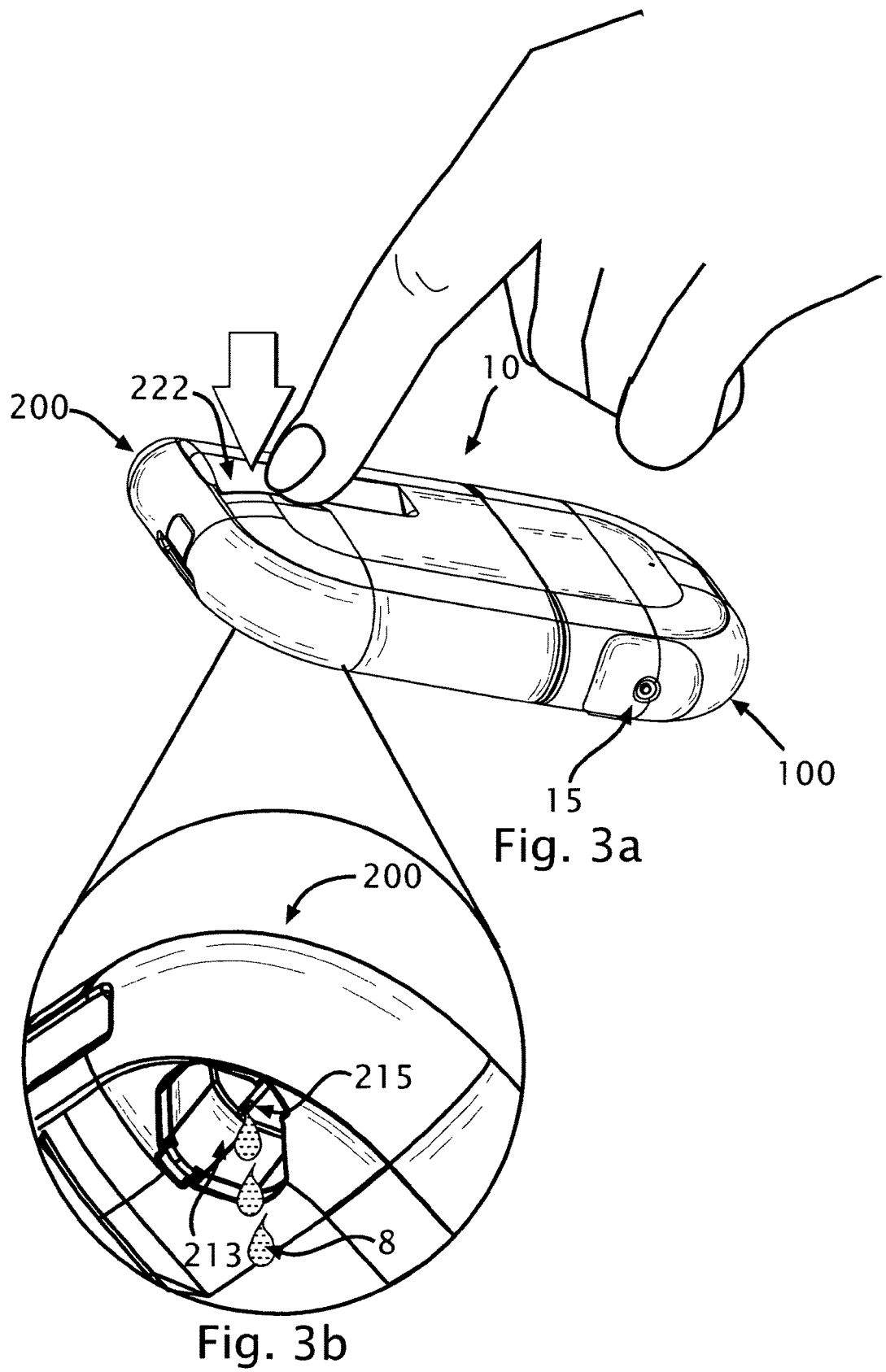
FIGS. 3a-3b are diagrams and views depicting external force exertion on the reservoir.

Referring to FIG. 3a, a diagram depicting the squeezing of the jeopardized zone 222 of a dispensing unit by an external force exertion is shown. The depicted dispensing unit 10 shows an assembled configuration, i.e., with the two parts of the dispensing unit 10 connected. The RP 100 includes one or more manual buttons 15. Referring to FIG. 3b, a magnified view of the bottom part of a DP 200 is shown. When subjected to force exertion that results in, for example, squeezing of the external surfaces of the dispensing unit 10, fluid drops 8 emerge from the connecting lumen 215 of the outlet port 213.

Figure 4:
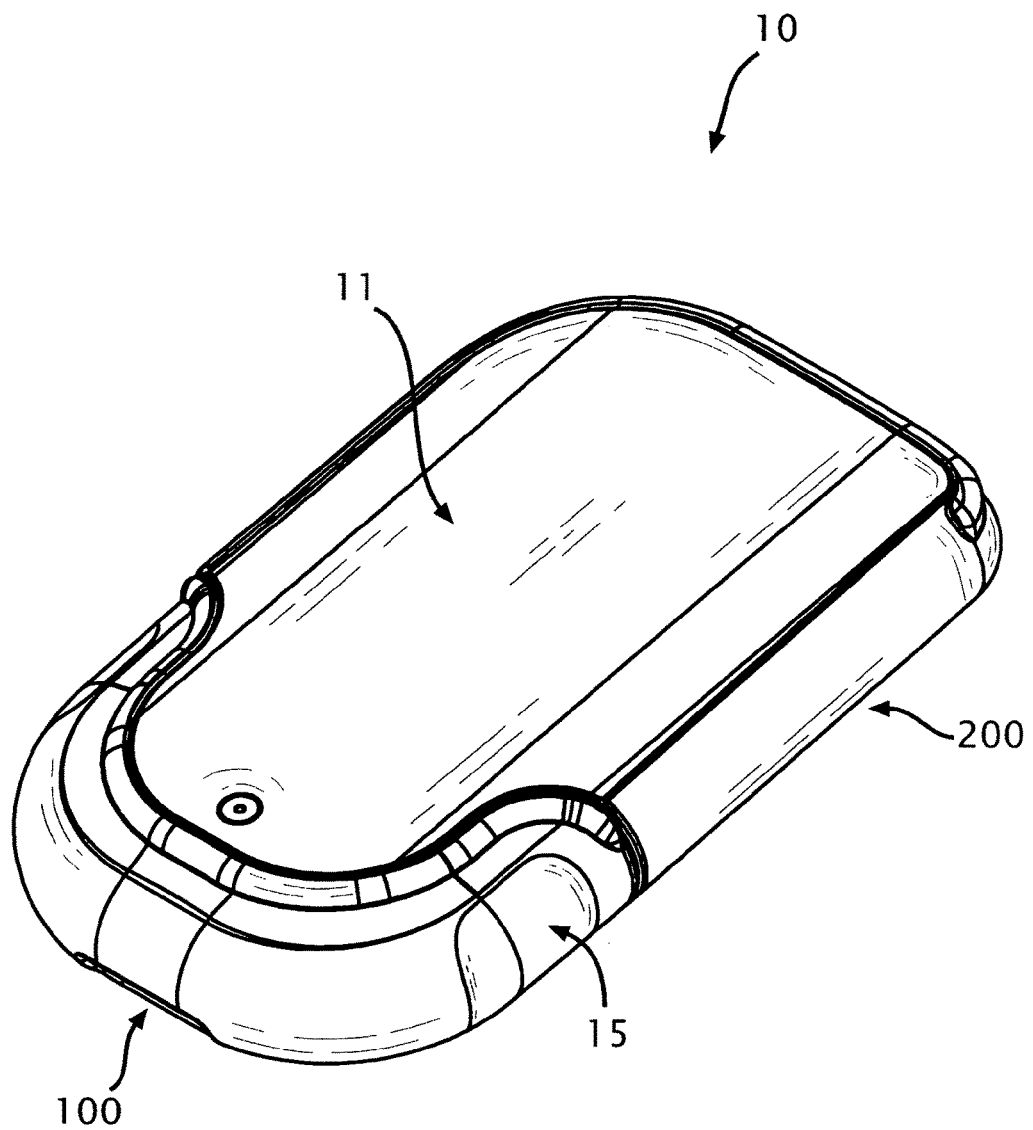
FIG. 4 is a diagram of a dispensing unit protected by a shield.

Referring to FIG. 4, a diagram of a dispensing unit 10 that includes a RP 100 and a DP 200, and covered with a protective shield 11, is shown. The shield 11 is coupled to an exterior face of the housing 250 and has a longest longitudinal length smaller than a longest longitudinal length of the housing 250 (additionally shown in FIG. 7A, for example). The protective shield 11 may be made of a hard/inflexible material, such as metal or polycarbonate that is relatively a robust material that is less vulnerable to external forces, and is adapted to divert external forces away from the jeopardized zone 222 (near which or within which the reservoir may reside) to a rigid structure (or "frame", not shown in FIG. 4) of the DP 200. In some embodiments, the shield 11 is configured to be substantially uncompromising such that forces applied to the disposable part 200, either within or outside the vicinity of the reservoir area, do not compromise the structure of the disposable part 200 and/or the reservoir 220. For example, the shield 11 could be used to "deflect" forces applied on the wall of the reservoir 220 which is covered by the shield 11.

Figure 5A:
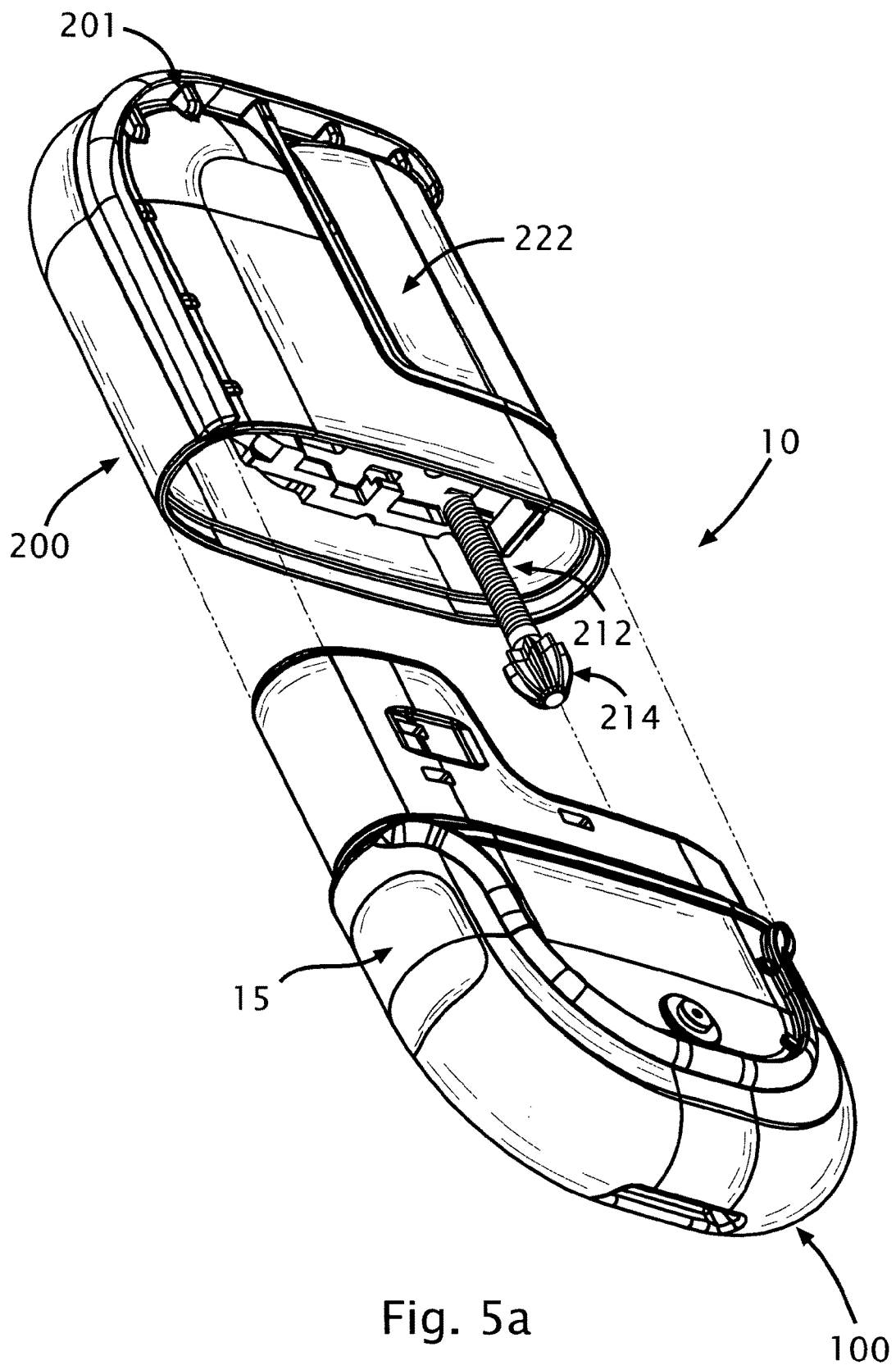
FIGS. 5a-5b are diagrams and views of a two-part dispensing unit before (FIG. 5a) and after (FIG. 5b) connection of a reusable part and a disposable part.
Figure 5B:
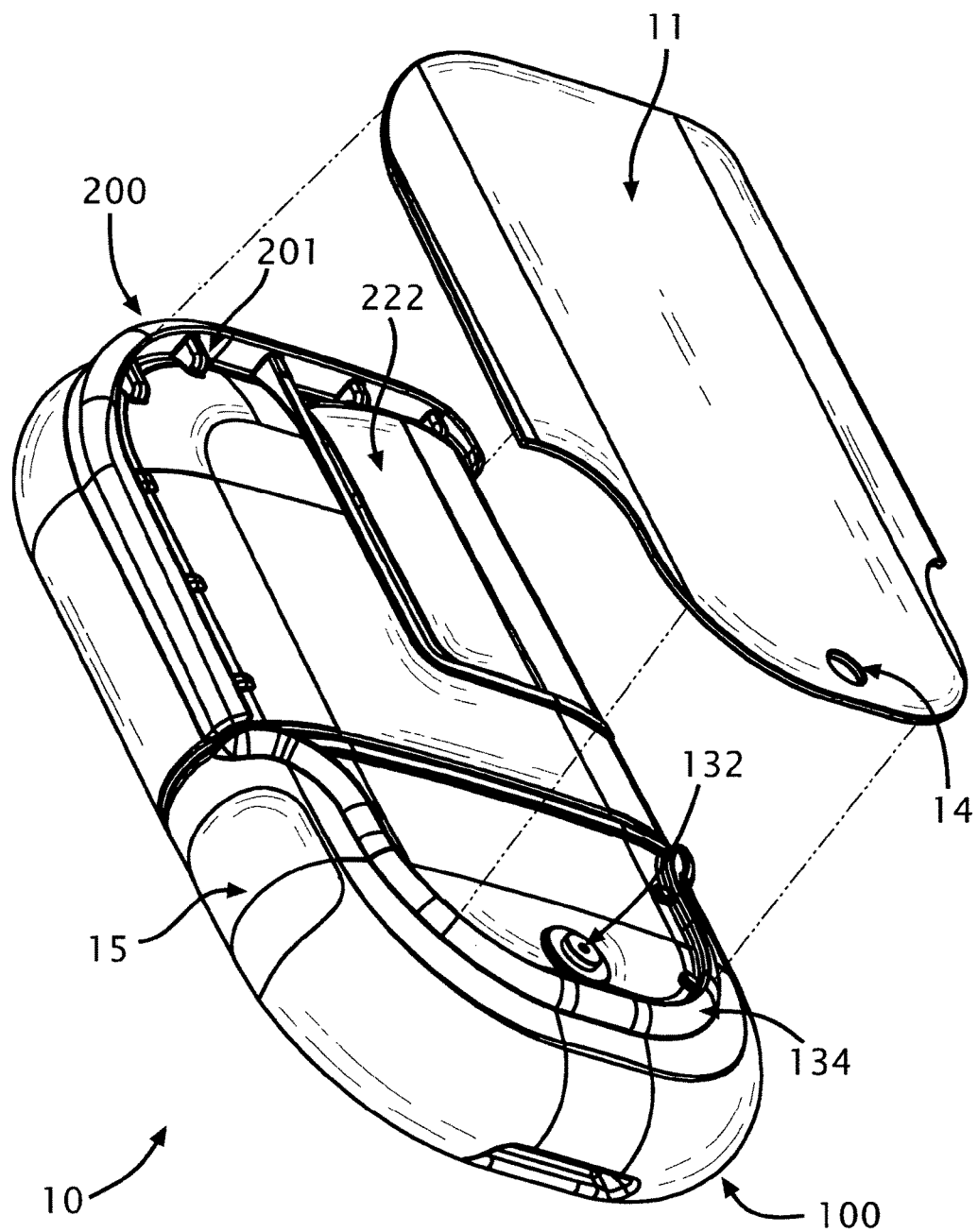

FIGS. 5a-5b show a two part dispensing unit 10 before (FIG. 5a) and after (FIG. 5b) connection of an RP 100 and a DP 200. FIG. 5a shows the RP 100 and the DP 200, which has a threaded piston rod 212 having a tip 214 (also referred to as "driving tip" or "juice extractor") with teeth/ribs at its proximal end. The tip 214 is engageable within a rotating gear (also referred-to as "sleeve", not shown in FIG. 5a) which is accommodated within the RP. The jeopardized zone 222 is surrounded at least in part by a frame 201 that has a rim and supporting ribs for receiving the shield (not shown in FIG. 5a) upon connection of the RP 100 to the DP 200. As shown in FIG. 5b, the shield 11 may be rigidly attached/secured to the RP 100 (e.g., by gluing), and it may be properly aligned (i.e., attached to the RP 100 such that upon connection of the RP 100 to the DP 200 the shield covers and protects the reservoir as required) using a protrusion 132 that fits into an opening 14 within the shield 11 and/or a rim 134 having a contour which substantially matches the contour of the proximal end of the shield, i.e., the end which is coupled to the RP. The shield 11 may be laid on (or received within) the rigid frame 201 to thus prevent exertion of direct pressure on the reservoir 220.

Figure 6:
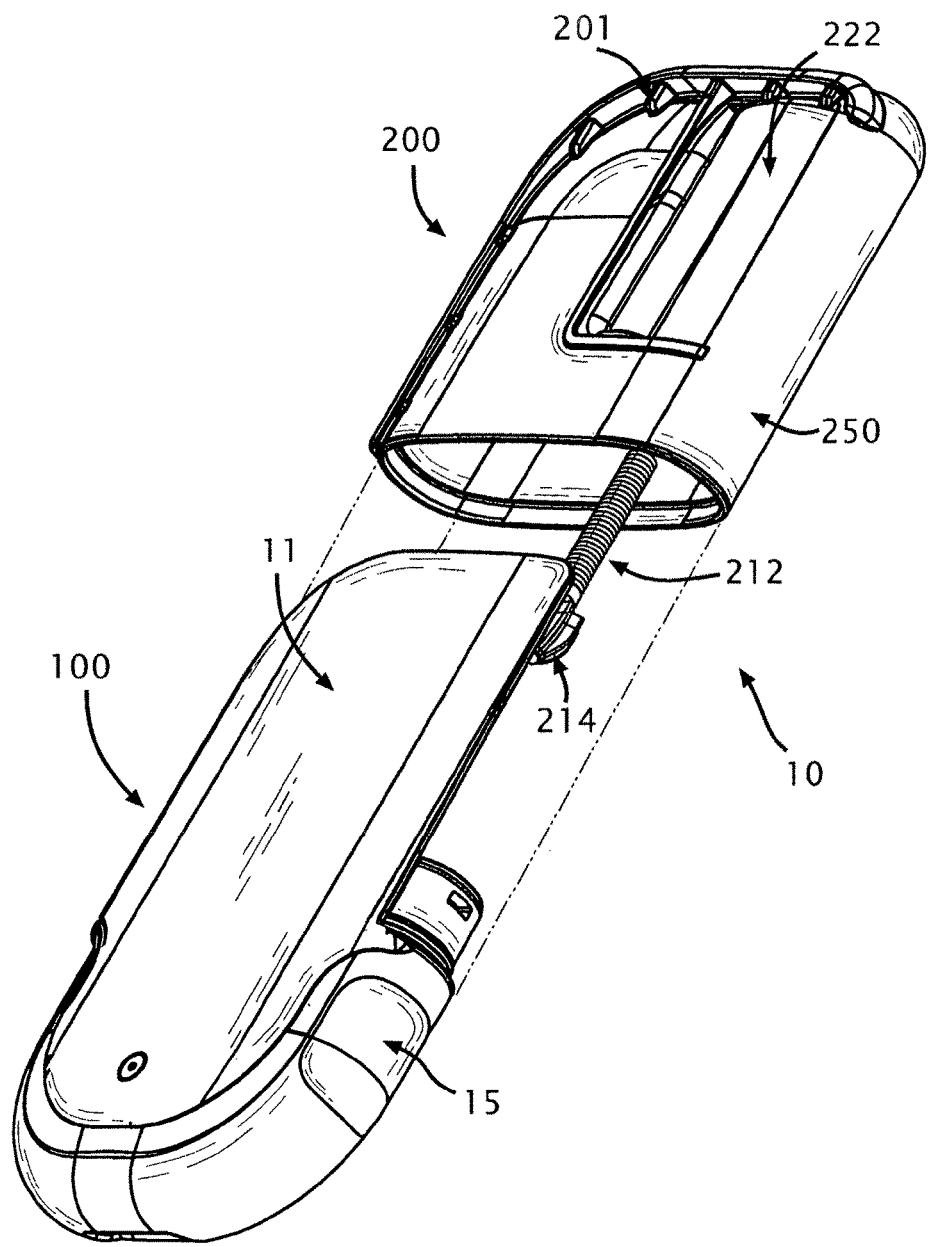
FIG. 6 is a diagram of a two-part dispensing unit and a shield connectable to a reusable part of the two-part dispensing unit.

FIG. 6 shows a two part dispensing unit 10 before connection of the RP 100 to a DP 200 having a threaded plunger rod 212 with a tip 214 ("juice extractor"). The protective shield 11 is attached/secured to the RP 100, and after connection of the RP 100 to the DP 200, the protective shield 11 is laid on (or rests on) the frame 201, thus covering and protecting the jeopardized zone 222. In some embodiments, the shield 11 is rigidly attached/secured to the RP 100 by gluing/adhesive, laser soldering, ultrasonic welding, or by manufacturing the shield 11 as an integral part of the housing of the RP or DP. In some embodiments, the housing/shell 250 (or at least a portion of the housing/shell) of the DP 200 may be made of a transparent material (e.g. polypropylene) to enable the user to inspect and monitor the content of the reservoir 220 (e.g. while filling the reservoir).

Figure 6A:
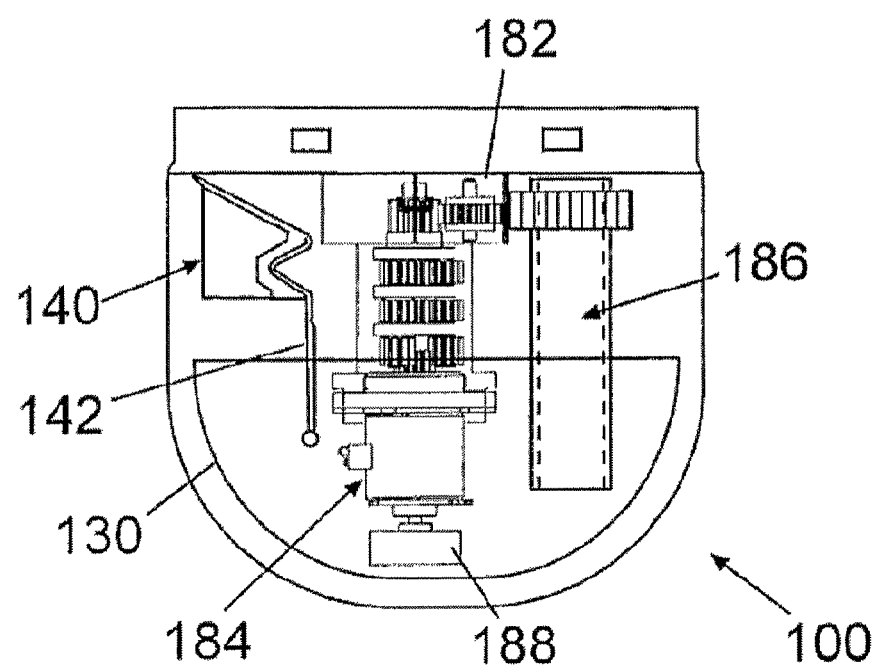
FIG. 6A is a diagram of a reusable part and its components.

Referring to FIG. 6A, a diagram of a reusable part 100 and its components is shown. The reusable part 100 includes at least a portion of a pump driving mechanism having a motor 184 and gears 182, which drive a threaded cylinder 186 (referred-to as a "sleeve" or "drive sleeve"). In some embodiments, the motor 184 can comprise a stepper motor, a DC motor, an SMA actuator, etc. The gears may include a unitary planetary gear, as shown in FIG. 6A, or any other power transmission mechanism such as a set of couplable cogwheels. The motor and/or gears can be coupled to one or more monitoring mechanisms (also referred to as monitoring units), such as a revolution counter or an encoder producing digital signals, or any other mechanism to monitor the operation of the driving mechanism, including the driving mechanism's motor, cogwheels and/or drive sleeve. The reusable part 100 can further comprise at least a portion of an occlusion sensor 140 with a sensing element 142 which is electrically connected to the Printed Circuit Board (PCB)/electronics 130 of the reusable part.

In some embodiments, the sleeve 186 is configured to receive the piston rod 212 of the disposable part 200 upon connection of the reusable part 100 and the disposable part 200, and to transfer rotational movement to the tip 214 of the piston rod 112 and the piston rod 112. The reusable part 100 may further includes electronics, designated with the reference numeral 130, and may comprise one or more of, for example, a controller, a processor, a transceiver, an antenna, etc.

Figure 7B:
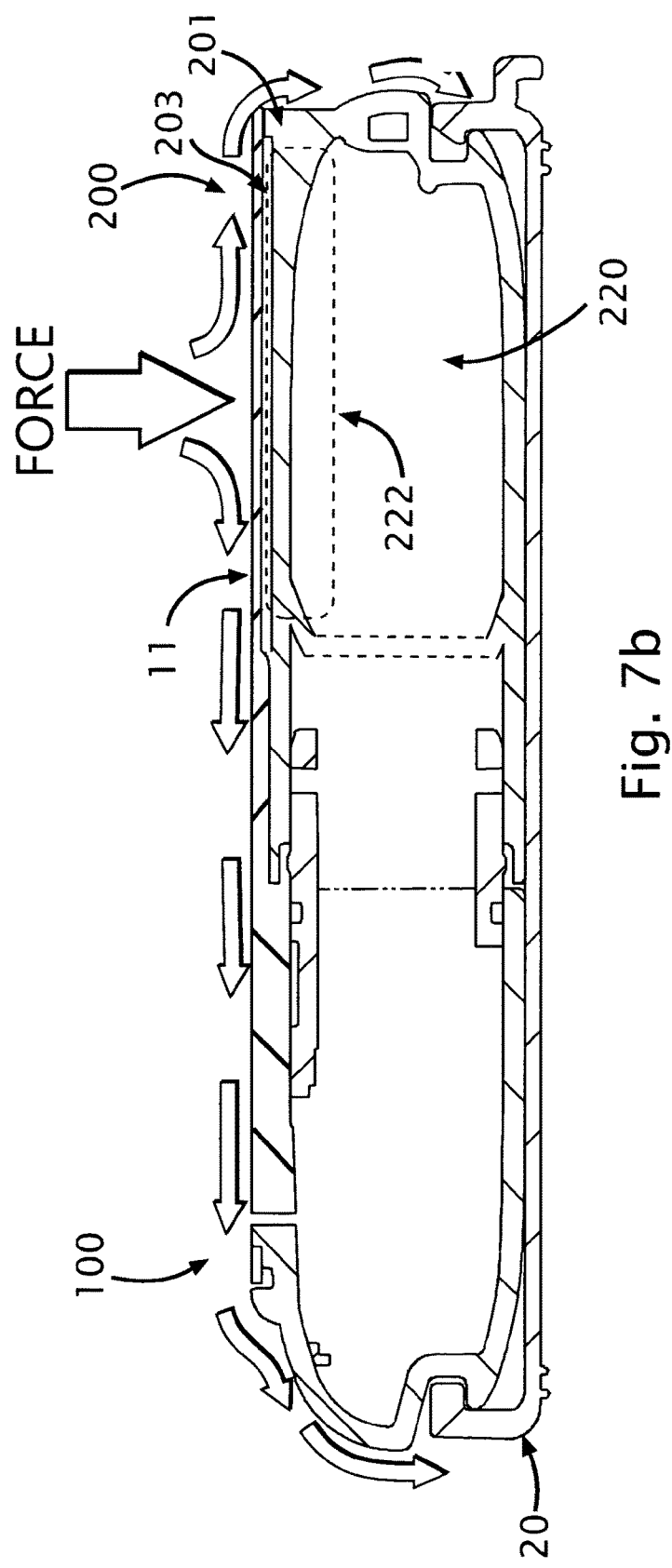

Referring to FIGS. 7a-7b, cross sectional views of a two part dispensing unit 10 (that includes, for example, an RP 100, and a DP 200 having a jeopardized zone 222) connected to the cradle 20 are shown. In some embodiments, the shield 11 is integrally connected to the RP 100 and is placed, at least in part, on the frame 201 that may be formed as an integral portion of the DP housing 250. A small air-gap 203 may separate the shield 11 and the reservoir 220 to protect against application of external forces (e.g., caused by pressing of a fingertip) directly onto the reservoir (as depicted in FIG. 7a). Applied forces are thus diverted away from the reservoir, as marked by the arrows in FIG. 7b, through the dispensing unit's edges and onto the cradle 20.

Figure 8A:
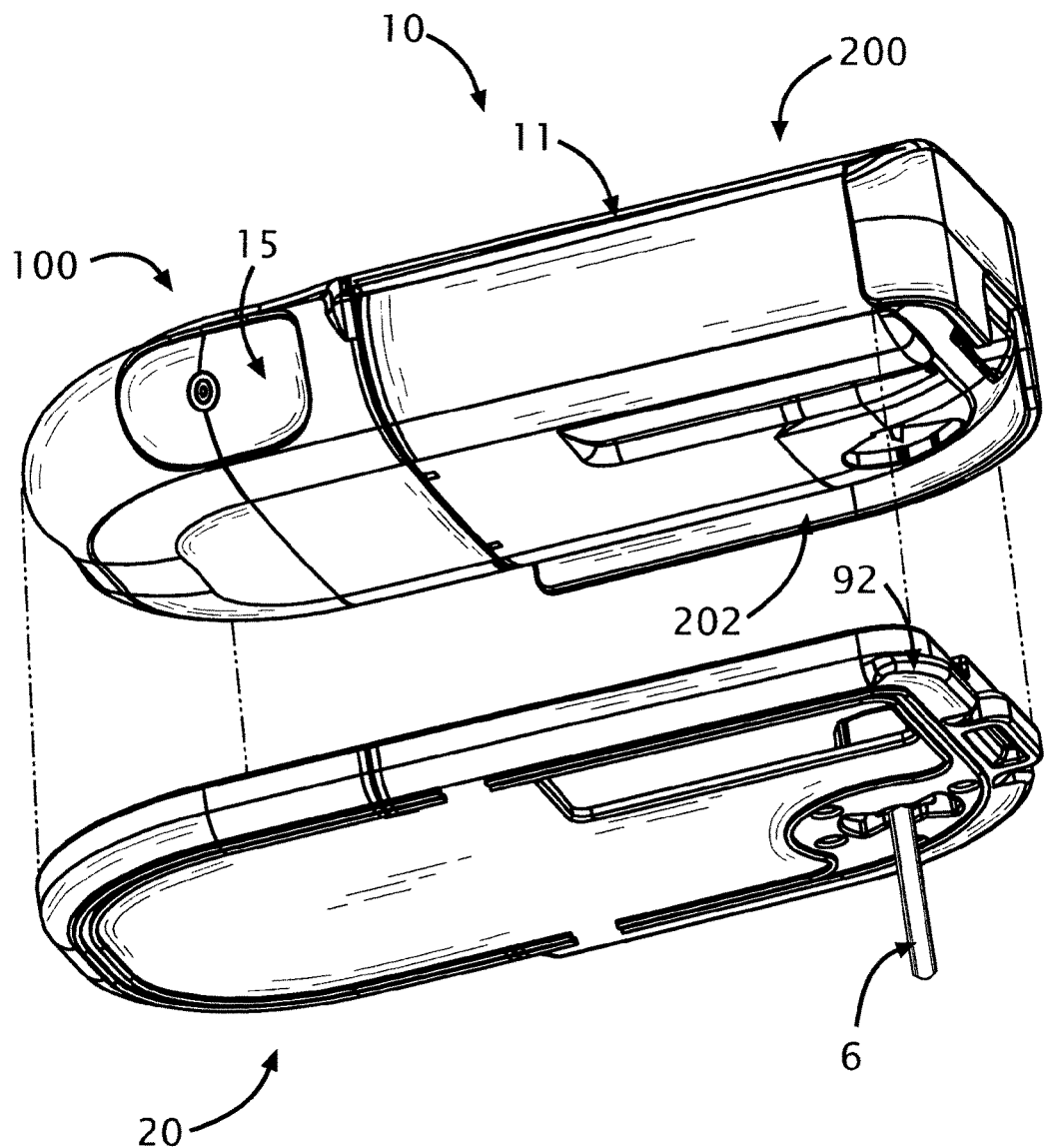
FIGS. 8a-8b are diagrams of a dispensing unit with a disposable part having a supporting frame onto which a shield can be placed so that external forces applied on the shield are conveyed to the cradle and diverted away from the reservoir.
Figure 8B:
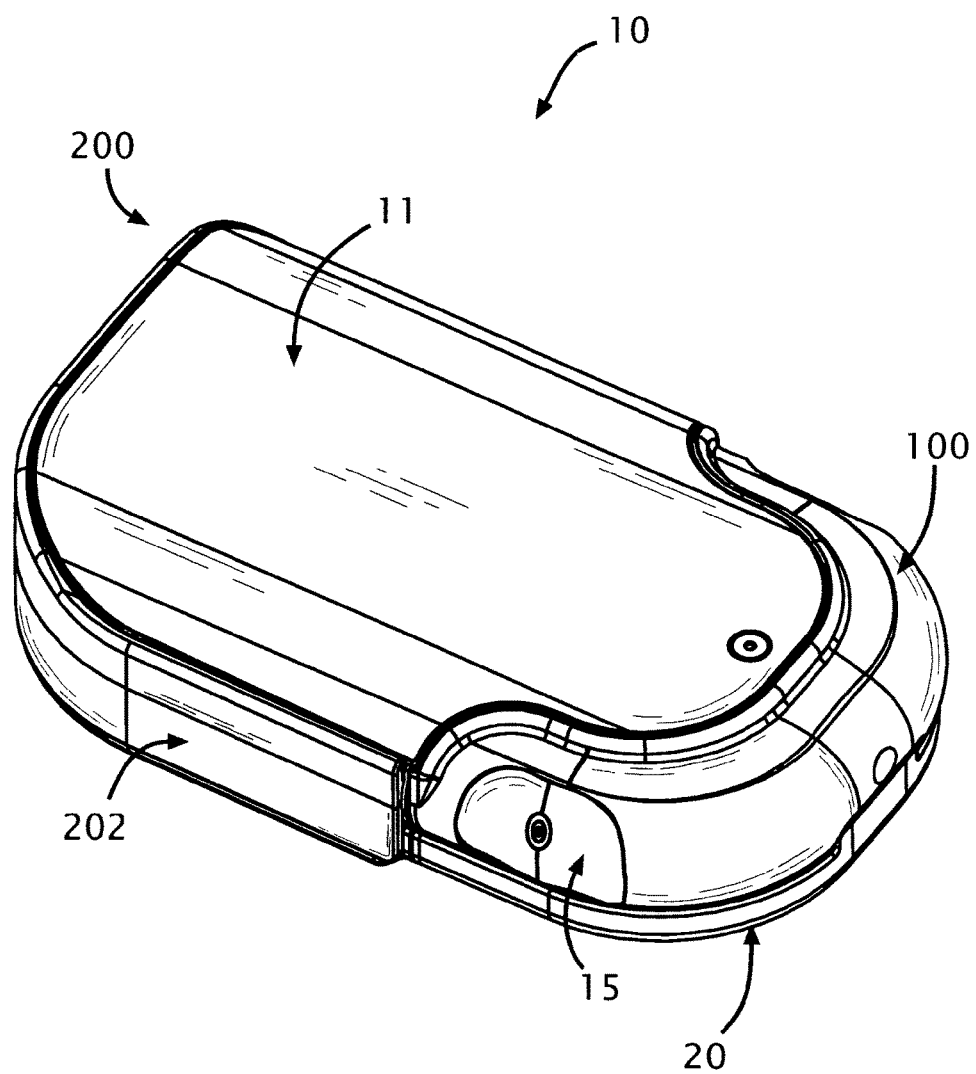

Referring to FIGS. 8a-8b, perspective views from different directions of a two-part dispensing unit 10 (assembled from an RP 100 and a DP 200) before (FIG. 8a) and after (FIG. 8b) connection to a cradle 20 with an inserted cannula 6 are shown. A DP lateral wall frame 202 protrudes above and below the reservoir (the reservoir itself is not shown in FIGS. 8a and 8b), supports and reinforces a shield 11, and diverts external forces onto cradle protrusions 92.

Figure 9:
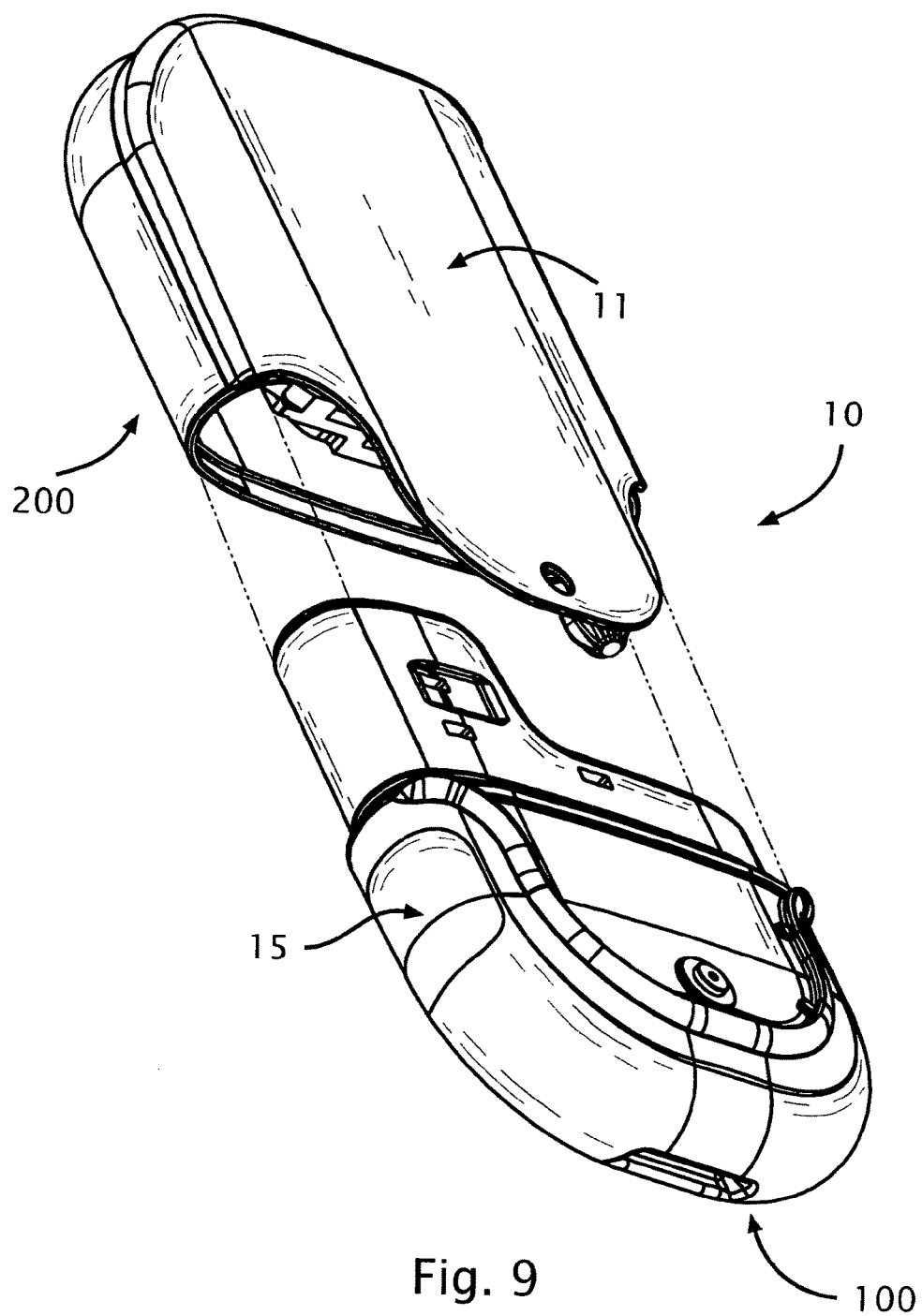
FIG. 9 is a diagram of another embodiment of a two-part dispensing unit with a shield attached to a disposable part of the dispensing unit.

Referring to FIG. 9, a view of a protective shield 11 that may be attached or secured to the DP 200 is shown. Upon connection of the DP 200 to the RP 100, the shield may be placed on the rigid RP case/housing.

Figure 10A:
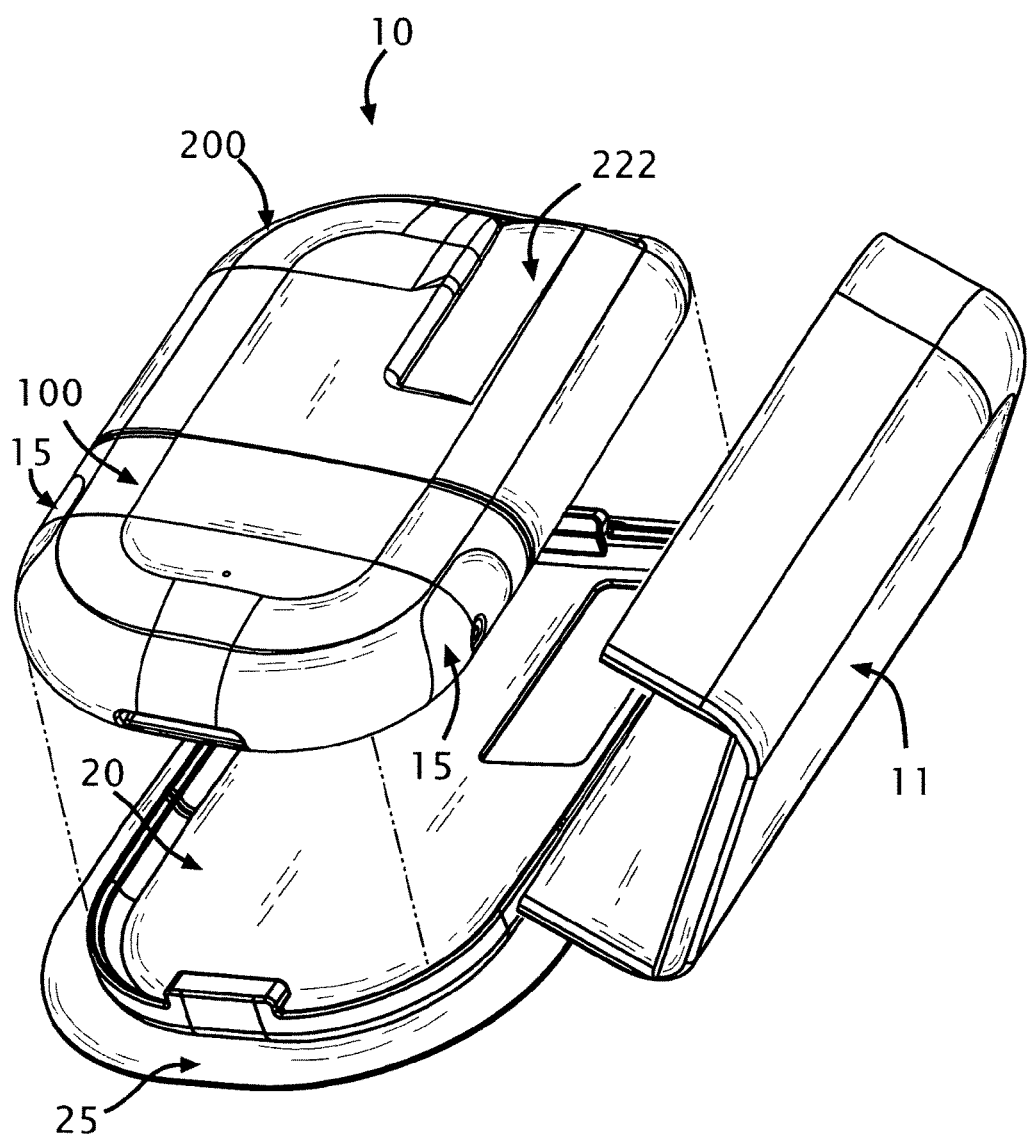
FIGS. 10a-10b are diagrams and views of another embodiment of an infusion device that includes a protective shield connected through a hinge to a cradle that receives a dispensing unit.
Figure 10B:
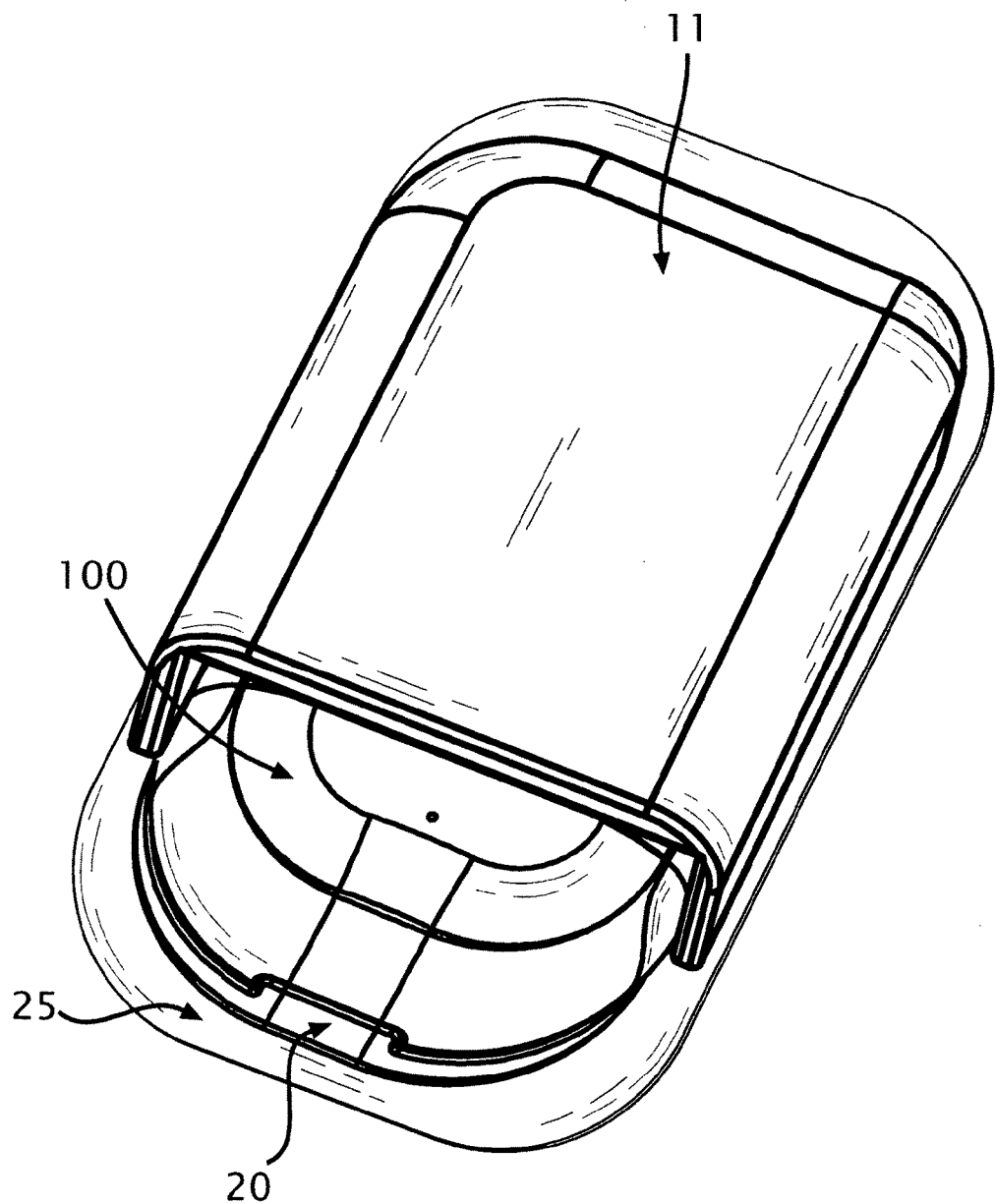

Referring to FIGS. 10a-10b, diagrams and views of a protective shield 11 which may be attached or secured to the cradle 20 are shown. In some embodiments, the shield may be formed as an integral portion of the cradle 20, e.g., by molded-injection. FIG. 10a shows a two-part dispensing unit 10 (including RP 100 and DP 200) before connection to the cradle 20. The cradle 20 comprises a securing mechanism to secure the cradle to the patient, e.g., an adhesive 25 on the bottom of the cradle, and the protective shield 11 that may be connected to the cradle 20 with a hinge (not shown), for example. FIG. 10b shows the dispensing unit 10 after connection to the cradle 20 and closing of the shield 11 over the dispensing unit 10. The shield 11 covering the DP 200 maintains a small air-gap from the reservoir (or from the jeopardized zone) to divert external forces away from the jeopardized zone to the cradle 20. The free side of the shield 11 (i.e., the side of the shield which is initially not connected to the cradle, as shown in FIG. 10a) may be mechanically secured to the cradle 20 by a locking mechanism, e.g., a latch-recess assembly (not shown). This locking mechanism (which may be different from the locking mechanism that connects the dispensing unit to the cradle) may be actuated by the user to release the protective shield 11 from its locking position to enable disconnection of the dispensing unit from the cradle.

Figure 11A:
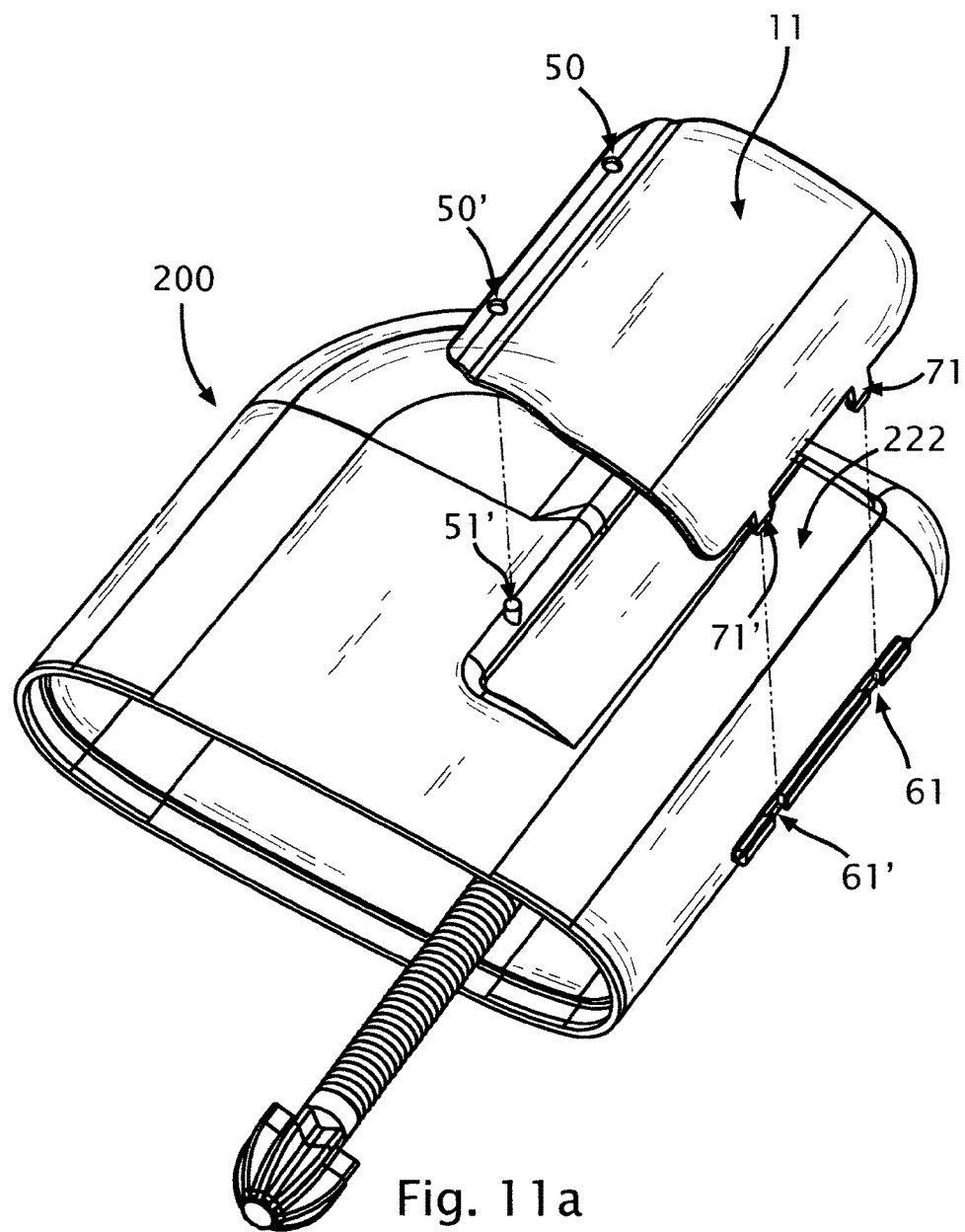
FIGS. 11a-11b are diagrams and views of another embodiment of an infusion device that includes a protective shield coupled to a support frame of a disposable part of a two-part dispensing unit of the infusion device.
Figure 11B:
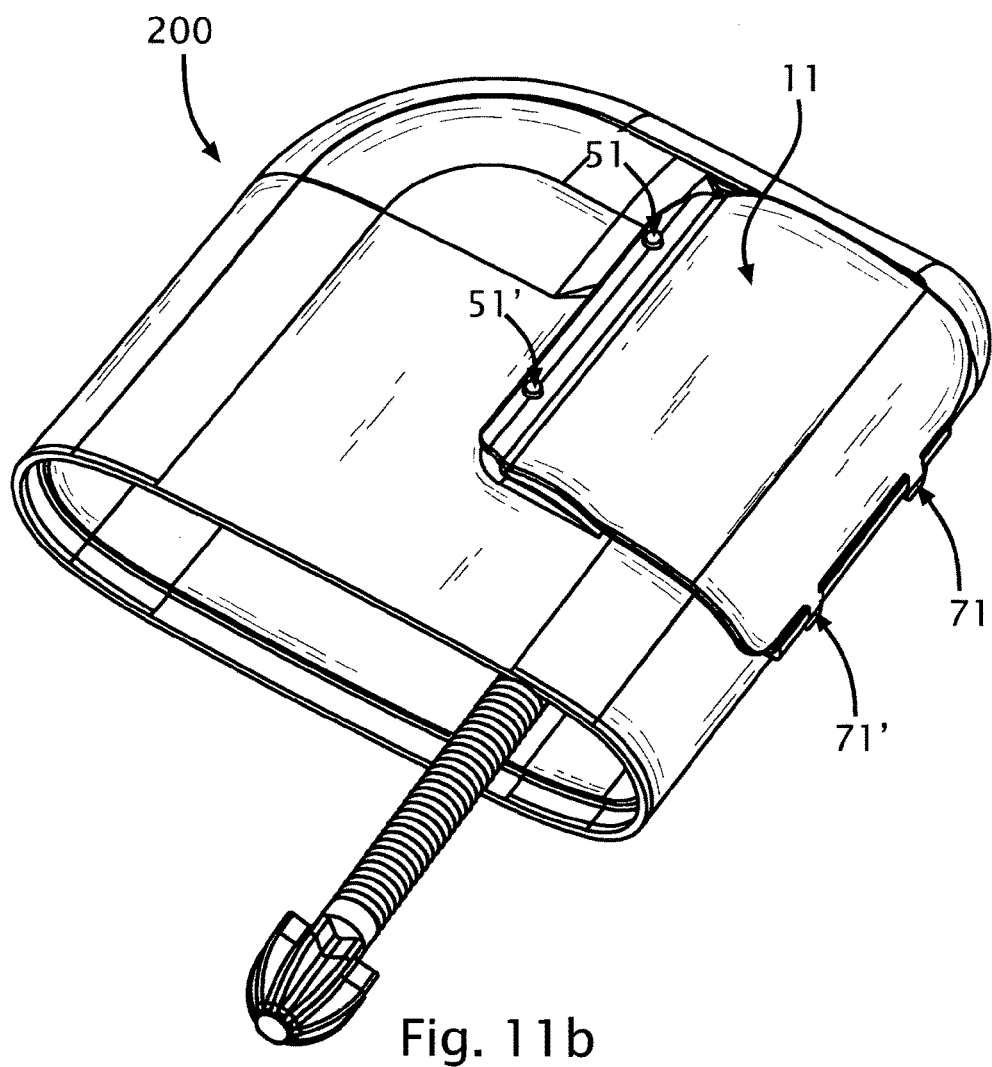

Referring to FIGS. 11*a*-11*b*, diagrams and views of an embodiment of a protective shield 11 which may be attached solely to a DP (i.e., the shield is not coupled to or does not otherwise come in contact or interact with the RP or the cradle) are shown. FIG. 11*a* shows the DP 200 including the jeopardized zone 222 before attachment of the protective shield 11. The DP 200 includes recesses 61, 61' created in the lateral side of the reservoir and protrusions 51, 51' (only protrusion 51' is shown in FIG. 11*a*) extending from the DP upper side for alignment with the shield's latches 71, 71' and openings 50, 50', respectively, to secure the shield 11 to the DP 200. FIG. 11*b* shows the shield 11 attached/secured to the DP 200 to thus enable the diversion of external forces away from the jeopardized zone 222.

In some embodiments, the shield 11 described above may further comprise an electronic platform that includes, for example, connectors and wiring to accommodate a battery's electrical connectors. In some embodiments, the shield 11 may accommodate a screen/display and/or buttons/switches/keypad to interact with the user.

In some embodiments, the shield may be made of such a material which prevents penetration of undesired radiation and/or energy (e.g., electromagnetic energy) from the surrounding into the dispensing unit, for example, RF radiation that could interfere and may damage communication processes to and from the dispensing unit, optical radiation penetration into the dispensing unit that may interfere/bias light-based detectors housed within the dispensing unit, etc. The shield may also be colored dedicatedly or formed with a specific texture to address these issues (e.g., using dark color to prevent penetration of light into the dispensing unit).

Various embodiments of the subject matter described herein may be realized in digital electronic circuitry, integrated circuitry, specially designed ASICs (application specific integrated circuits), computer hardware, firmware, software, and/or combinations thereof. These various embodiments may include embodiment in one or more computer programs that are executable and/or interpretable on a programmable system including at least one programmable processor, which may be special or general purpose, coupled to receive data and instructions from, and to transmit data and instructions to, a storage system, at least one input device, and at least one output device. Some embodiments include specific "modules" which may be implemented as digital electronic circuitry, integrated circuitry, specially designed ASICs (application specific integrated circuits), computer hardware, firmware, software, and/or combinations thereof.

Computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable. Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the subject matter described herein may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

Some or all of the subject matter described herein may be implemented in a computing system that includes a back-end component (e.g., as a data server), or that includes a middleware component (e.g., an application server), or that includes a front-end component (e.g., a client computer having a graphical user interface or a Web browser through which a user may interact with an embodiment of the subject matter described herein), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Any and all references to publications or other documents, including but not limited to, patents, patent applications, articles, webpages, books, etc., presented in the present application, are herein incorporated by reference in their entirety.

Although particular variations have been disclosed herein in detail, this has been done by way of example for purposes of illustration only, and is not intended to be limiting with respect to the scope of the appended claims, which follow. In particular, it is contemplated that various substitutions, alterations, and modifications may be made without departing from the spirit and scope of the invention as defined by the claims. Other aspects, advantages, and modifications are considered to be within the scope of the following claims. The claims presented are representative of the embodiments and features disclosed herein. Other unclaimed embodiments and features are also contemplated. Accordingly, other embodiments are within the scope of the following claims.

The invention claimed is:

1. A therapeutic fluid dispenser comprising:
   a reservoir for storing a therapeutic fluid;
   a pump driving mechanism having a motor;
   a dispenser housing configured to accommodate the reservoir and the pump driving mechanism;
   a shield directly coupled to an exterior face of the dispenser housing, the shield having a longest longitudinal length smaller than a corresponding length of the dispenser housing and configured to protect, at least in part, the reservoir from one or more external forces acting on the shield, the shield being spaced from the reservoir to define an air gap therebetween; and
   a cradle removably connected to the dispenser housing, the cradle including an adhesive layer on one or more surfaces of the cradle to adhere to a skin of a patient and a passageway for subcutaneously inserting a cannula therethrough.

2. The dispenser according to claim 1, wherein the dispenser housing comprises at least one protrusion receivable within a corresponding at least one opening provided on the shield to enable proper alignment of the shield.

3. The dispenser according to claim 1, wherein the dispenser housing comprises a frame configured and arranged to support the shield and space the shield at a distance from the reservoir.

4. The dispenser according to claim 3, wherein the frame is further configured to divert the one or more external forces away from the dispenser housing.

5. The dispenser according to claim 1, wherein the dispenser housing defines at least a portion of the reservoir.

6. The dispenser according to claim 1, wherein the dispenser housing defines at least a wall of the reservoir, the air gap being defined between the shield and the wall of the reservoir defined by the dispenser housing.

7. The dispenser according to claim 1, wherein the dispenser housing comprises:
a first housing configured to accommodate at least a portion of the pump driving mechanism; and
a second housing coupleable to the first housing, the second housing being configured to accommodate at least a portion of the reservoir;
wherein the shield is coupleable to at least one of the first housing or the second housing.

8. The dispenser according to claim 1, wherein the dispenser housing is provided with a rim having a contour substantially matching a contour defined by edges of the shield to enable proper alignment of the shield.

9. The dispenser according to claim 1, wherein the shield is further configured to divert the one or more external forces to the cradle.

10. The dispenser according to claim 1, wherein the shield is rigidly attached to the dispenser housing via one or more of: gluing, laser soldering, ultrasonic welding, and manufacturing the shield as an integral part of the at least one housing.

11. The dispenser according to claim 1, wherein the shield is made of a material selected from a group consisting of metal, polycarbonate, and a combination of the foregoing.

12. The dispenser according to claim 1, wherein the shield is configured to protect the dispenser from radiation.

13. The dispenser according to claim 1, wherein the shield is removable from the dispenser housing.

14. A therapeutic fluid dispenser comprising:
a first part including:
at least a portion of a pump driving mechanism having a motor; and
a first housing configured to accommodate the at least a portion of the pump driving mechanism;
a second part coupleable to the first part, the second part including:
a reservoir for retaining a therapeutic fluid; and
a second housing configured to accommodate the reservoir;
a shield directly coupled to an exterior face of the first housing and having a longest longitudinal length smaller than a corresponding length of a dispenser housing comprising the first housing and the second housing;
wherein the shield is spaced from the reservoir to define an air gap therebetween, and configured to protect, at least in part, the reservoir from one or more external forces thereon when the first part and the second part are coupled,
wherein the first housing comprises at least one protrusion receivable within a corresponding at least one opening provided on the shield to enable proper alignment of the shield, and
wherein the second housing comprises a frame configured to support the shield such that the shield is not in direct contact with the reservoir.

15. A therapeutic fluid dispenser comprising:
a first part including:
at least a portion of a pump driving mechanism having a motor; and
a first housing configured to accommodate the at least a portion of the pump driving mechanism;
a second part coupleable to the first part, the second part including:
a reservoir for retaining a therapeutic fluid; and
a second housing configured to accommodate the reservoir;
a shield directly coupled to an exterior face of the first housing and having a longest longitudinal length smaller than a corresponding length of a dispenser housing comprising the first housing and the second housing;
wherein the shield is spaced from the reservoir to define an air gap therebetween, and configured to protect, at least in part, the reservoir from one or more external forces thereon when the first part and the second part are coupled, and
wherein the shield is rigidly attached to the first housing and extends beyond a length of the first housing to protect the reservoir when the first part and the second part are coupled.

* * * * *